United States Patent [19]

Conrow et al.

[11] Patent Number: 4,608,205

[45] Date of Patent: Aug. 26, 1986

[54] POLYANIONIC BENZENE UREAS

[75] Inventors: Ransom B. Conrow, Pearl River; Seymour Bernstein, New City, both of N.Y.

[73] Assignee: American Cyanamid Company, Stamford, Conn.

[21] Appl. No.: 653,400

[22] Filed: Sep. 24, 1984

Related U.S. Application Data

[63] Continuation-in-part of Ser. No. 473,412, Mar. 9, 1983, abandoned, which is a continuation-in-part of Ser. No. 274,860, Jun. 18, 1981, abandoned.

[51] Int. Cl.$^4$ .................. C07C 143/52; C07C 143/54
[52] U.S. Cl. ................................... 260/506
[58] Field of Search .............. 260/506, 501.19, 501.17, 260/501.1, 501.16, 501.21; 562/439; 546/184, 347; 544/410

[56] References Cited

U.S. PATENT DOCUMENTS

| | | | |
|---|---|---|---|
| 2,806,062 | 9/1957 | Gehauf et al. | 564/55 |
| 3,679,420 | 7/1972 | Yokoyama | 260/506 |
| 4,177,209 | 12/1979 | Conrow et al. | 260/506 |

OTHER PUBLICATIONS

Ettel et al., Chem. Abstr., 69, 26953n (1968) Abstract of Collect. Czech. Chem. Commun., 33, 1948, (1968).
Ettel et al., Chem. Abstr., 94, 174670z (1981) Abstr. of Czech Pat. No. 182,853, (4–15–80).
Kozyukov et al., C.A., 91, 20,592b (1979).
Rhone-Poulene, C.A., 67, 81,969f, (1967) Abstract of Neth. Appl. No. 6,607,601.

*Primary Examiner*—Nicky Chan
*Attorney, Agent, or Firm*—Susan H. Rauch; A. M. Rosenblum

[57] ABSTRACT

Polyanionic benzene ureas and salts thereof useful as complement inhibitors.

2 Claims, No Drawings

POLYANIONIC BENZENE UREAS

CROSS REFERENCE TO RELATED APPLICATION

This application is a continuation-in-part of our copending application, Ser. No. 473,412, filed Mar. 9, 1973, now abandoned; which is a continuation-in-part of Ser. No. 274,860, filed June 18, 1981, now abandoned.

BACKGROUND OF THE INVENTION

1. Field of Invention

The present invention relates to novel polyanionic benzene ureas and salts thereof and their use as inhibitors of the complement system of warm-blooded animals.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W.H.O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 454, 592, 642 (1972); Sci. Am. 229 (5): 54 (1973); Fed. Proc. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976-1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestion regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 15: 813 (1978); J. Biol. Chem. 254; 9908 (1979)

A variety of substances have been disclosed as inhibiting the complement system, i.e., as complement inhibitors. For example, the compounds, 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim.

Biophys. Acta 317: 539 (1973); Life Sci. 13: 351 (1973); J. Immunol. 113: 584 (1974); Immunology 26: 819 (1974); J. Med. Chem. 17: 1160 (1974); Biochim. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23:240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

This invention relates to polyanionic benzene ureas which interact with the complement reaction sequence, thereby inhibiting complement activity in body fluids.

DETAILED DESCRIPTION OF THE INVENTION

This invention is concerned with new compounds of Formula I:

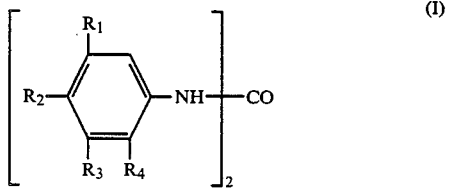

(I)

wherein $R_1$ is selected from the group consisting of hydrogen, —COOH and —$SO_3A$; $R_2$ is selected from the group consisting of hydrogen, hydroxy, —COOH, chlorine, fluorine and bromine; $R_3$ is selected from the group consisting of hydrogen, —COOH and —$SO_3A$; $R_4$ is selected from the group consisting of hydrogen and —$SO_3A$; and A is a nontoxic pharmaceutically acceptable salt cation, wherein the salt forming moiety is selected from the group consisting of alkali metal, alkaline earth metal, ammonia and substituted ammonia selected from the group consisting of trialkylamine ($C_1$-$C_6$), piperidine, pyrazine, alkanolamine ($C_2$-$C_6$) and cycloalkylamine ($C_3$-$C_6$), with the proviso that at least one member of $R_1$, $R_2$, $R_3$ and $R_4$ is —COOH or —$SO_3A$; that when $R_1$ is —COOH and $R_2$ is hydroxy, then $R_3$ or $R_4$ must be other than hydrogen; and that when $R_3$ is —COOH and $R_2$ is hydroxy, then $R_1$ or $R_4$ must be other than hydrogen.

This invention is also concerned with a method of inhibiting the complement system in a body fluid, such as blood serum, which comprises subjecting body fluid complement to the action of an effective complement inhibiting amount of a compound of the above Formula. Body fluids can include blood, plasma, serum, synovial fluid, cerebrospinal fluid, or pathological accumulations of fluid such as pleural effusion, etc. This invention is further concerned with a method of inhibiting the complement system in a warm-blooded animal which comprises administering to said animal an effective complement inhibiting amount of a compound of the above Formula.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as, for example, inflammation following coronary occlusion. They may also be useful in the treatment of transplant rejection and ulcers and as blood culture and transport mediums. The compounds additionally may be employed in treatment of periodontal diseases such as periodontitis or gingivitis and related diseases of the oral cavity.

Particularly preferred compounds of this invention which are of major interest as complement inhibitors include the following:

4,4'-Ureylenebis(2-sulfobenzoic acid), disodium salt 3,3'-(Carbonyldiimino)bis(6-hydroxy-5-sulfobenzoic acid), disodium salt.

The compounds of the present invention are prepared according to the following flowchart:

FLOWCHART

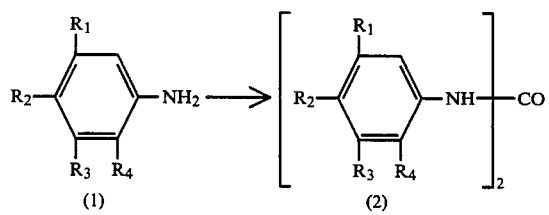

General Procedure

Phosgene is bubbled into a vigorously stirred and cooled aqueous solution or aqueous acetone solution of the amino acid (1) and base (sodium hydroxide or sodium carbonate) (at a ratio of 2-5 moles of base per mole of amine) until the solution is acidic (pH 1-2), wherein $R_1$ is selected from the group consisting of hydrogen, —COOH and —SO$_3$A; $R_2$ is selected from the group consisting of hydrogen, hydroxy, —COOH, chlorine, fluorine and bromine; $R_3$ is selected from the group consisting of hydrogen, —COOH and —SO$_3$A; $R_4$ is selected from the group consisting of hydrogen and —SO$_3$A; and A is a nontoxic pharmaceutically acceptable salt cation, wherein the salt forming moiety is selected from the group consisting of alkali metal, alkaline earth metal, ammonia and substituted ammonia selected from the group consisting of trialkylamine (C$_1$-C$_6$), piperidine, pyrazine, alkanolamine (C$_2$-C$_6$) and cycloalkylamine (C$_3$-C$_6$). The reaction is monitored by thin-layer electrophoresis or thin-layer chromatography. If required, more sodium carbonate is added and phosgenation is repeated until the mixture is acidic. The mixture is made weakly basic with sodium hydroxide or sodium carbonate and the excess hydroxide or carbonate is neutralized with acetic acid. The solution is filtered and the filtrate is warmed and diluted with ethanol to precipitate the product (2), wherein $R_1$, $R_2$, $R_3$ and $R_4$ are defined as above. The mixture is cooled, the solid is collected by filtration, washed successively with aqueous ethanol, then absolute ethanol and finally with ether and dried at 110° C.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also, it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g., toxicity, effectiveness, etc.) of the parent compound. The salts of the present invention which are pharmaceutically acceptable include the alkali metals (e.g., sodium, potassium, etc); alkaline earth metals (e.g., calcium, etc.); ammonia; and substituted ammonia selected from the group consisting of trialkylamine (C$_1$-C$_6$), piperidine, pyrazine, alkanolamine (C$_2$-C$_6$) and cycloalkylamine (C$_3$-C$_6$).

The term "trialkylamine (C$_1$-C$_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine (C$_2$-C$_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine (C$_3$-C$_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 20° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

A further understanding of the invention can be obtained from the following non-limiting Preparations and Examples.

EXAMPLE 1

5,5'-Ureylenedi-m-benzenedisulfonic acid, tetrasodium salt

Phosgene was bubbled through a solution of 10.0 g of 5-amino-1,3-benzenedisulfonic acid disodium salt and 7.1 g of anhydrous sodium carbonate in 70 ml of water until the solution was acidic (pH 1-2). An additional 1.0 g of sodium carbonate was added and phosgenation was repeated until the solution was acidic. The solution was made weakly basic with sodium carbonate and the excess carbonate was neutralized with acetic acid. The solution was filtered and the filtrate was warmed and diluted with ethanol until a precipitate was obtained. The mixture was cooled, the solid was collected, washed with aqueous ethanol, then absolute ethanol and finally with ether and dried at 110° C., giving 7.8 g of the desired product as a colorless powder.

EXAMPLE 2

4,4'-Ureylenebis(2-sulfobenzoic acid), disodium salt

To a mixture of 50.6 g of 5-nitro-o-toluenesulfonic acid, 300 ml of water and 40 ml of 5N sodium hydroxide, heated on a steam bath, was added a hot solution of 80 g of potassium permanganate in 500 ml of water. The mixture was heated intermittently on the steam bath and an additional 25 g of potassium permanganate was added over the course of 2.5 hours. The mixture was filtered and washed with water and the combined filtrate and wash was concentrated to about 200 ml and then cooled. The solid was collected by filtration and washed with water, ethanol and ether. The filtrate was concentrated to about 100 ml giving additional solid. These solids were combined, added to a mixture of 200 ml of water and 16 ml of concentrated hydrochloric acid and heated on a steam bath. This solution was diluted with 300 ml of ethanol and allowed to stand overnight. The solid was collected, washed with 50% aqueous ethanol, ethanol, then ether and dried overnight at 110° C., giving 32.75 g of 4-nitro-2-sulfobenzoic acid, 2-sodium salt.

A mixture of 2.84 g of the above compound, 20 ml of water, 2.0 ml of 5N sodium hydroxide and 500 mg of palladium on carbon was hydrogenated for 3.5 hours and then filtered. To this filtrate was added 2.12 g of anhydrous sodium carbonate and the mixture was phosgenated until acidic, heated to effect solution and cooled. The solid was collected, washed with ice water, ethanol, then ether and dried overnight at 110° C., giving 2.15 g of the desired product as a colorless powder.

EXAMPLE 3

3,3'-Ureylenebis(6-chlorobenzenesulfonic acid), disodium salt

A mixture of 8.32 g of 5-amino-2-chlorobenzenesulfonic acid, 21 g of anhydrous sodium carbonate and 100 ml of water was phosgenated as described in Example 1. The solid was recrystallized from water containing 200 mg of added sodium hydroxide, giving 8.82 g of the desired product.

EXAMPLE 4

2,2'-Ureylenedibenzenesulfonic acid, disodium salt

A mixture of 6.92 g of o-aminobenzenesulfonic acid, 21 g of anhydrous sodium carbonate and 75 ml of water was phosgenated as described in Example 1, giving 4.04 g of the desired product.

EXAMPLE 5

5,5'-Ureylenediisophthalic acid, tetrasodium salt

A mixture of 12.0 g of 5-aminoisophthalic acid, 28 ml of 5N sodium hydroxide, 14 g of anhydrous sodium carbonate and 250 ml of water was phosgenated as described in Example 1, giving 6.0 g of the desired product.

EXAMPLE 6

3,3'-(Carbonyldiimino)bis(6-hydroxy-5-sulfobenzoic acid), disodium salt

A solution of 5.5 g of 3-amino-6-hydroxy-5-sulfobenzoic acid, 20 ml of 5N sodium hydroxide, 5 ml of water and 25 ml of acetone was treated with phosgene until acidic. The solid was collected, washed with water and dried by azeotroping with ethanol and then heating at 110° C. overnight. This solid was further purified by heating with ethanol on a steam bath, filtering and concentrating the ethanol solution, giving 4.16 g of the desired product as a gray powder.

EXAMPLE 7

Preparation of Compressed Tablet

| Ingredient | mg/Tablet |
| --- | --- |
| Active Compound | 0.5–500 |
| Dibasic Calcium Phosphate NF | qs |
| Starch USP | 40 |
| Modified Starch | 10 |
| Magnesium Stearate USP | 1–5 |

EXAMPLE 8

Preparation of Compressed Tablet—Sustained Action

| Ingredient | mg/Tablet |
| --- | --- |
| Active Compound as Aluminum Lake*, Micronized | 0.5–500 (as acid equivalent) |
| Dibasic Calcium Phosphate NF | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 9

Preparation of Hard Shell Capsule

| Ingredient | mg/Capsule |
| --- | --- |
| Active Compound | 0.5–500 |
| Lactose, Spray Dried | qs |
| Magnesium Stearate | 1–10 |

EXAMPLE 10

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 11

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 12

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 13

Preparation of Injectable Solution

| Ingredient | % W/V |
| --- | --- |
| Active Compound | 0.05–5 |
| Benzyl Alcohol NF | 0.9 |
| Water for Injection | 100.0 |

EXAMPLE 14

Preparation of Injectable Oil

| Ingredient | % W/V |
| --- | --- |
| Active Compound | 0.05–5 |
| Benzyl Alcohol | 1.5 |
| Sesame Oil qs ad | 100.0 |

EXAMPLE 15

Preparation of Intra-Articular Product

| Ingredient | Amount |
| --- | --- |
| Active Compound | 2–20 mg |
| NaCl (physiological saline) | 0–9% |
| Benzyl Alcohol | 0.9 |

| Ingredient | Amount |
| --- | --- |
| Sodium Carboxymethylcellulose | 1.5% |
| pH adjusted to 5.0–7.5 | |
| Water for Injection qs ad | 100% |

EXAMPLE 16

Preparation of Injectable Depo Suspension

| Ingredient | % W/V |
| --- | --- |
| Active Compound | 0.05–5 |
| | (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

EXAMPLE 17

Preparation of Dental Paste

| Ingredient | % W/W |
| --- | --- |
| Active Compound | 0.05–5 |
| Zinc Oxide | 15 |
| Polyethylene Glycol 4000 USP | 50 |
| Distilled Water qs | 100 |

EXAMPLE 18

Preparation of Dental Ointment

| Ingredient | % W/W |
| --- | --- |
| Active Compound | 0.05–5 |
| Petrolatum, White USP qs | 100 |

EXAMPLE 19

Preparation of Dental Cream

| Ingredient | % W/W |
| --- | --- |
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 20

Preparation of Topical Cream

| Ingredient | % W/W |
| --- | --- |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |

| Ingredient | % W/W |
| --- | --- |
| Purified Water qs | 100 |

EXAMPLE 21

Preparation of Topical Ointment

| Ingredient | % W/W |
| --- | --- |
| Active Compound | 0.05–5 |
| Cholesterol | 3 |
| Stearyl Alcohol | 3 |
| White Wax | 8 |
| Petrolatum, White USP qs | 100 |

EXAMPLE 22

Preparation of Spray Lotion (Non-aerosol)

| Ingredient | % W/W |
| --- | --- |
| Active Compound | 0.05–5 |
| Isopropyl Myristate | 20 |
| Alcohol (Denatured) qs | 100 |

EXAMPLE 23

Preparation of Buccal Tablet

| Ingredient | mg/Tablet |
| --- | --- |
| Active Ingredient | 3.25 |
| 6 × Sugar | 290.60 |
| Acacia | 14.53 |
| Soluble Starch | 14.53 |
| F. D. & C. Yellow No. 6 Dye | 0.49 |
| Magnesium Stearate | 1.60 |
| | 325.00 |

The final tablet will weigh about 325 mg and may be compressed into buccal tablets in flat faced or any other tooling shape convenient for buccal administration.

EXAMPLE 24

Preparation of Lozenge

| Ingredient | g/Lozenge |
| --- | --- |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity. These dental compositions may be therapeutically applied during the early stages of periodontal disease commonly known as gingivitis.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by the following identified test: Test Code 026 (C1 inhibitor)—This test measures the ability of activated human C1 to destroy fluid phase human C2 in the presence of C4 and appropriate dilutions of the test compound. An active inhibitor protects C2 from C1 and C4. Table I shows that the representative compounds of this invention possess highly significant complement inhibiting activity in warm-blooded animals.

TABLE I

| Biological Activities | |
|---|---|
| Compound | Cl 026* Wells |
| 3,3'-(Carbonyldiimino)bis(6-hydroxy-5-sulfobenzoic acid), disodium salt | +2** |
| 4,4'-Ureylenebis(2-sulfobenzoic acid), disodium salt | +2 |

*Test identified by code herein.
**Activity in wells, a serial dilution assay. Higher well number indicates higher activity. The serial dilutions are two-fold.

We claim:
1. The compound 4,4-ureylenebis(2-sulfobenzoic acid), disodium salt.
2. The compound 3,3-(carbonyldiimino)bis(6-hydroxy-5-sulfobenzoic acid), disodium salt.

* * * * *